(12) United States Patent
Futatsuyama et al.

(10) Patent No.: US 8,774,896 B2
(45) Date of Patent: Jul. 8, 2014

(54) ELECTROCARDIOGRAPH WITH SUBJECT CONTACT DETECTION BASED ON SIGNAL DIFFERENCE

(75) Inventors: Kouki Futatsuyama, Anjo (JP); Tsuyoshi Nakagawa, Aichi-gun (JP); Harutsugu Fukumoto, Anjo (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 13/596,213

(22) Filed: Aug. 28, 2012

(65) Prior Publication Data

US 2013/0060120 A1    Mar. 7, 2013

(30) Foreign Application Priority Data

Sep. 5, 2011   (JP) ................................. 2011-192920

(51) Int. Cl.
  *A61B 5/0402*   (2006.01)
(52) U.S. Cl.
  USPC .......................................... 600/393; 600/509
(58) Field of Classification Search
  USPC ................... 600/393, 509; 702/104
  See application file for complete search history.

(56) References Cited

U.S. PATENT DOCUMENTS

| 7,684,854 | B2 * | 3/2010 | Park et al. ...................... 600/509 |
| 2004/0260190 | A1 | 12/2004 | Tanabe et al. |
| 2005/0143666 | A1 | 6/2005 | Yanaga |
| 2006/0004295 | A1 * | 1/2006 | Prydekker ...................... 600/509 |
| 2011/0125002 | A1 * | 5/2011 | Ershov et al. .................. 600/384 |
| 2011/0251817 | A1 * | 10/2011 | Burns et al. .................... 702/104 |

FOREIGN PATENT DOCUMENTS

| JP | A-H07-194562 | 8/1995 |
| JP | A-H07-275218 | 10/1995 |
| JP | A-H11-178804 | 7/1999 |
| JP | A-H11-347006 | 12/1999 |
| JP | A-2003-180643 | 7/2003 |
| JP | B2-3906703 | 4/2007 |
| JP | A-2009-118999 | 6/2009 |

* cited by examiner

*Primary Examiner* — Christopher D Koharski
*Assistant Examiner* — Michael Carey
(74) *Attorney, Agent, or Firm* — Posz Law Group, PLC

(57) ABSTRACT

An electrocardiograph includes first and second induction electrodes, a signal difference generation section, an electrocardiographic detection section, a signal applying section, and a contact detection section. The signal difference generation section generates a potential difference between a signal from the first induction electrode and a signal from the second induction electrode as a signal difference. The electrocardiographic detection section detects an electrocardiographic complex of a subject based on the signal difference. The signal applying section applies a first signal to the first induction electrode and a second signal to the second induction electrode. The first signal has a property different from the electrocardiographic complex. The second signal has a property different from the electrocardiographic complex and the first signal. The contact detection section detects a contact state of the subject to the first and second induction electrodes based on the signal difference.

15 Claims, 7 Drawing Sheets

ELECTROCARDIOGRAPH WITH SUBJECT CONTACT DETECTION BASED ON SIGNAL DIFFERENCE

CROSS REFERENCE TO RELATED APPLICATION

This application is based on Japanese Patent Application No. 2011-192920 filed on Sep. 5, 2011, the disclosure of which is incorporated herein by reference.

TECHNICAL FIELD

The present disclosure relates to an electrocardiograph.

BACKGROUND

An electrocardiograph used for detecting an electrocardiographic complex of a person, such as a driver, in a vehicle has been known. Such an electrocardiograph detects the electrocardiographic complex of the person (hereinafter referred to as the subject) by measuring an electric potential difference generated between induction electrodes disposed in a steering wheel.

To properly detect the electrocardiographic complex of the subject by using such an electrocardiograph, the electrocardiograph needs to realize that the body of the subject is in contact with each of the induction electrodes. As a method of realizing that the body is in contact with each of the induction electrodes, it is considered to simulate an electrocardiographic complex and to apply a signal (hereinafter referred to as the simulation noise signal) whose signal level is higher than a predetermined level to one of the induction electrodes. Such a method is described in JP-B2-3906703, for example.

FIG. 8A shows an assumed electrocardiograph 100 for a vehicle, which employs the method described in JP-B2-3906703. The assumed electrocardiograph 100 includes a first induction electrode ER1, a second induction electrode EL1, a first indifferent electrode IR1, and a second indifferent electrode IL1. The first induction electrode ER1 and the first indifferent electrode IR1 are paired with each other, and are located in an area of a steering wheel SW1 held with the right hand of the subject. Likewise, the second induction electrode EL1 and the second indifferent electrode IL1 are paired with each other, and are located in an area of a steering wheel SW1 held with the left hand of the subject. The assumed electrocardiograph 100 applies a simulation noise signal Sn to the second induction electrode ER1.

As shown in FIG. 8B, the assumed electrocardiograph 100 further includes a differential amplifying circuit 101, a filter 102 and an amplifier 103. The differential amplifying circuit 101 outputs an electric potential difference between a signal outputted from the first induction electrode ER1 and a signal outputted from the second induction electrode EU. The amplifier 103 amplifies the output of the differential amplifying circuit 101 after passing through the filter 102.

In the assumed electrocardiograph 100, in a state where the subject does not hold the steering wheel SW1, an impedance between the first induction electrode ER1 and the second induction electrode EU is infinity. Therefore, an output from the amplifier 103 has a value corresponding to the signal level of the simulation noise signal Sn.

On the other hand, in a state where the subject holds the steering wheel SW1 with both hands, the impedance between the first induction electrode ER1 and the second induction electrode EU becomes small. Therefore, the output from the amplifier 103 has a value lower than the signal level of the simulation noise signal Sn. Accordingly, the assumed electrocardiograph 100 can determine whether the steering wheel SW is held with both the hands or not.

However, in a state where the subject holds the steering wheel SW1 with only the left hand, the output from the amplifier 103 has a value lower than the signal level of the simulation noise signal Sn. Therefore, the assumed electrocardiograph 100 will erroneously determine that the steering wheel WS is held with both the hands.

Namely, it is difficult to properly detect that the body of the subject is in contact with both of the first induction electrode ER1 and the second induction electrode EU by the assumed electrocardiograph 100.

SUMMARY

It is an object of the present disclosure to provide an electrocardiograph capable of determining that a body of a subject is in contact with each of induction electrodes.

According to an aspect of the present disclosure, an electrocardiograph includes first and second induction electrodes, first and second reference electrodes as indifferent electrodes, a signal difference generation section, an electrocardiographic detection section, a signal applying section and a contact detection section. The first induction electrode induces a first signal applied thereto. The second induction electrode induces a second signal applied thereto. The first reference electrode is associated with the first induction electrode, and the second reference electrode is associated with the second induction electrode. The signal difference generation section generates a potential difference between a signal outputted from the first induction electrode and a signal outputted from the second induction electrode as a signal difference. The electrocardiographic detection section detects an electrocardiographic complex of a subject based on the signal difference generated by the signal difference generation section. The signal applying section applies the first signal to the first induction electrode and the second signal to the second induction electrode. The first signal has a property different from the electrocardiographic complex. The second signal has a property different from the electrocardiographic complex and the first signal. The contact detection section detects a contact state of the subject to the first induction electrode and the second induction electrode based on the signal difference generated by the signal difference generation section.

In the configuration described above, when the body of the subject is in contact with the first induction electrode and the second induction electrode, the first induction electrode is electrically connect to the first reference electrode through the body of the subject, and the second induction electrode is electrically connected to the second reference electrode through the body of the subject. At this time, an impedance between the first induction electrode and the first reference electrode and an impedance between the second induction electrode and the second reference electrode become small. Therefore, the signal difference becomes a potential corresponding to a potential of the electrocardiographic complex.

On the other hand, when the body of the subject Hm is not in contact with the first induction electrode and the second induction electrode, the first induction electrode is not electrically connected to the first reference electrode, and the second induction electrode is not electrically connected to the second reference electrode. Therefore, the impedance between the first induction electrode and the first reference electrode, and the impedance between the second induction electrode and the second reference electrode are maintained to infinity. As a result, the signal difference becomes a difference between a potential corresponding to the first signal and a potential corresponding to the second signal.

When the body of the subject is in contact with the first induction electrode without contacting the second induction electrode, the impedance between the first induction electrode and the first reference electrode becomes small, but the impedance between the second induction electrode and the second reference electrode is maintained to infinity. Therefore, the signal difference becomes the potential corresponding to the second signal.

Also, when the body of the subject is in contact with the second induction electrode without contacting the first induction electrode, the impedance between the first induction electrode and the first reference electrode is maintained to infinity, but the impedance between the second induction electrode and the second reference electrode becomes small. Therefore, the signal difference becomes the potential corresponding to the first signal.

Namely, the signal difference is different according to a contact state of the body of the subject to the first induction electrode and the second induction electrode. Accordingly, it is possible to determine that the body of the subject is in contact with each of the first induction electrode and the second induction electrode.

BRIEF DESCRIPTION OF THE DRAWINGS

The above and other objects, features and advantages of the present disclosure will become more apparent from the following detailed description made with reference to the accompanying drawings, in which like parts are designated by like reference numbers and in which.

DETAILED DESCRIPTION

Exemplary embodiments of the present disclosure will be described hereinafter with reference to the drawings.

(First Embodiment)

Figure 1:
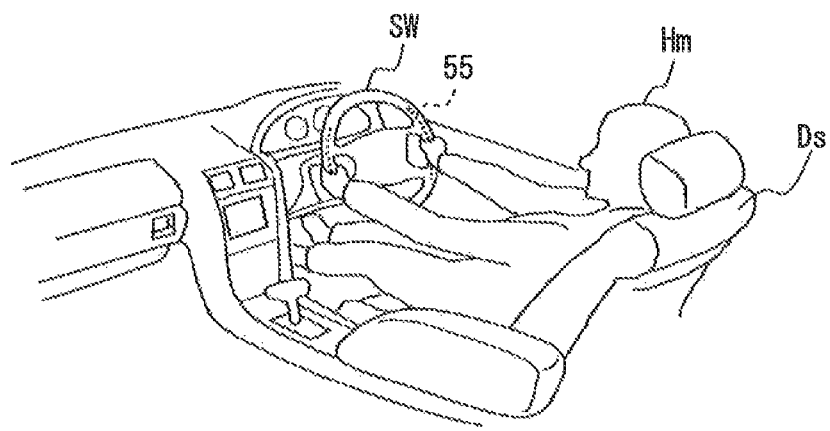
FIG. 1 is a diagram illustrating a schematic view of a driver's seat of a vehicle and a steering wheel equipped with electrodes of an electrocardiograph according to a first embodiment of the present disclosure.
Figure 2:
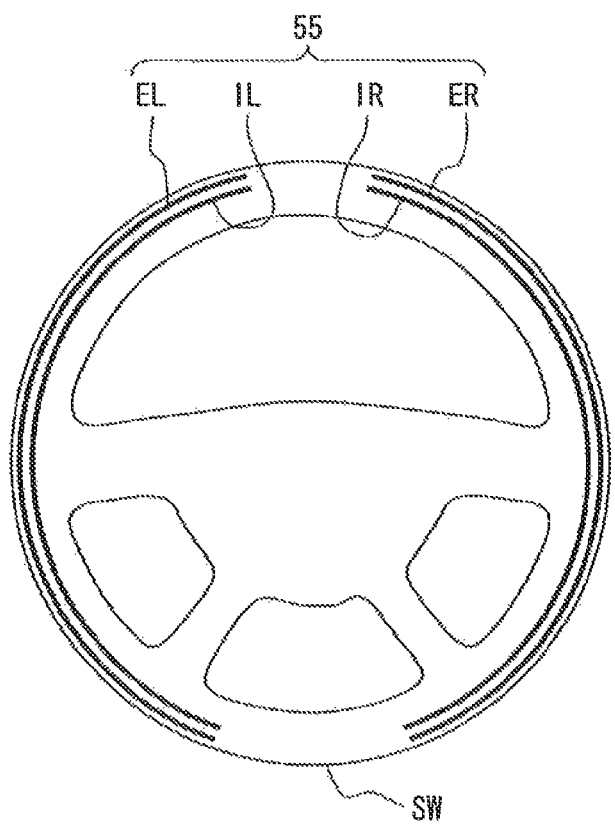
FIG. 2 is a diagram illustrating a plan view of the steering wheel equipped with the electrodes of the electrocardiograph according to the first embodiment.
Figure 3:
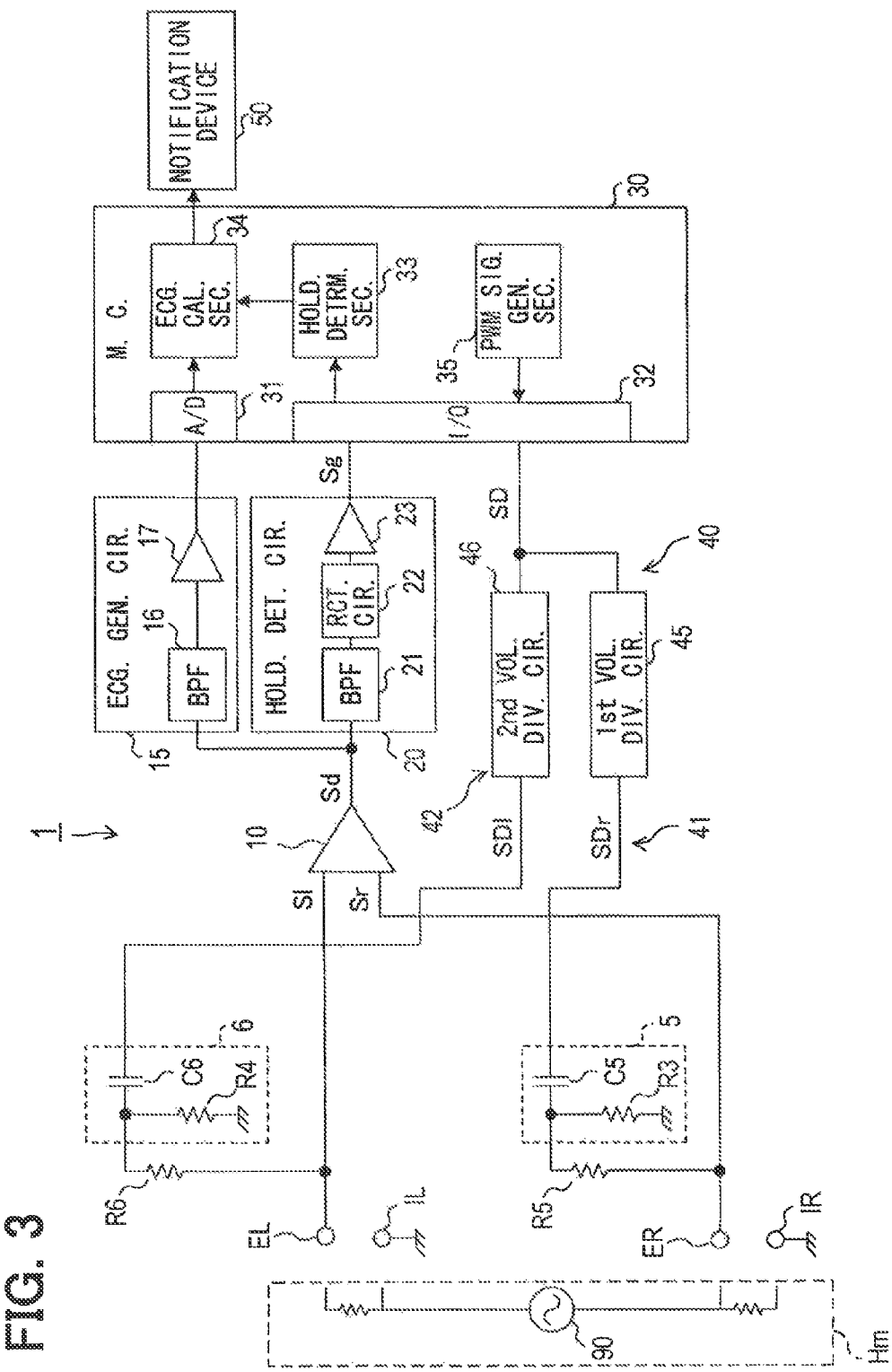
FIG. 3 is a block diagram of the electrocardiograph according to the first embodiment.

Referring to FIGS. 1 through 3, an electrocardiograph 1 according to the first embodiment is disposed in a vehicle to detect an electrocardiographic complex of a subject Hm. The subject Hm is a person seated on a driver's seat Ds. In general, the subject Hm is a driver of the vehicle. In FIG. 3, a heart 90 of the subject Hm is exemplarily illustrated by an AC power source.

It is to be noted that the electrocardiographic complex of the present disclosure corresponds to an electric signal that causes a human's heart to beat, and in which cardiac potential changes periodically in the shape of pulse. Specifically, the electrocardiographic complex is a signal made of "P wave", "Q wave", "R wave", "S wave", "T wave" and the like of one heartbeat as one cycle.

<Electrodes>

As shown in FIG. 1, the electrocardiograph 1 includes an electrode unit 55 disposed on a steering wheel SW of a vehicle. As shown in FIG. 2, the electrode unit 55 includes a first induction electrode ER, a second induction electrode EL, a first reference electrode IR, and a second reference electrode IL. The first and second induction electrodes ER, EL are provided to induce signals inputted thereto. The first and second reference electrodes IR, IL are provided as indifferent electrodes.

The first induction electrode ER and the first reference electrode IR are disposed in an area of the steering wheel SW held with the right hand. The second induction electrode EL and the second reference electrode IL are disposed in an area of the steering wheel SW held with the left hand.

The first reference electrode IR is associated with the first induction electrode ER. The first reference electrode IR is disposed adjacent to the first induction electrode ER so that a part of the body of the subject Hm contacts the first induction electrode ER as well as the first reference electrode IR.

The second reference electrode IL is associated with the second induction electrode EL. The second reference electrode IL is disposed adjacent to the second induction electrode EL so that a part of the body of the subject Hm contacts the second induction electrode EL as well as the second reference electrode IL.

<Main Structure>

Next, a main structure of the electrocardiograph 1 will be described with reference to FIG. 3.

In addition to the electrode unit 55, the electrocardiograph 1 includes a detection signal input unit 40, and a differential amplifier 10. The detection signal input unit 40 is configured to input a detection signal SD to the first induction electrode ER and the second induction electrode EL. The detection signal SD has a frequency higher than a frequency of a signal that is detected from the subject Hm as the electrocardiographic complex. The differential amplifier 10 is configured to output a differential signal Sd indicative of a difference between a signal Sr outputted from the first induction electrode ER and a signal SI outputted from the second induction electrode EL.

The electrocardiograph 1 further includes an electrocardiographic complex generation circuit 15 and a holding-state detection circuit 20. The electrocardiographic complex generation circuit 15 is configured to generate the electrocardiographic complex of the subject Hm based on the differential signal Sd outputted from the differential amplifier 10. The holding-state detection circuit 20 is configured to generate a holding signal Sg based on the differential signal Sd outputted from the differential amplifier 10. The holding signal Sg indicates a holding state of the steering wheel SW, that is, how the steering wheel SW is held by the subject Hm.

The electrocardiograph 1 further includes a microcomputer 30 and a notification device 50. The microcomputer 30 determines the holding state of the steering wheel SW based on the holding signal Sg. Also, the microcomputer 30 generates biological information indicative of a condition of the subject Hm based on the electrocardiographic complex. The notification device 50 notifies the biological information generated by the microcomputer 30.

For example, the notification device 50 includes a display unit for displaying the information and a sound output unit for outputting the information by a sound. For example, the display unit includes a liquid crystal display, and the sound output unit includes a speaker device.

The microcomputer 30 includes at least a ROM, a RAM, and a CPU. The ROM stores data and a program that need to be memorized even if a power supply to the microcomputer 30 is turned off. The RAM temporarily stores data. The CPU performs a processing according to the program memorized in the ROM or the RAM. The microcomputer 30 further includes an AND converter 31 that converts an analog signal into a digital signal, and an I/O port 32 that is an interface used for inputting and outputting of information.

The microcomputer 30 further includes a holding-state determination section 33, an electrocardiographic calculation section 34 and a PWM signal generation section 35. The holding-state determination section 33 determines the holding state of the steering wheel SW based on the holding signal Sg transmitted from the holding-state detection circuit 20 through the I/O port 32. The electrocardiographic calculation section 34 generates the electrocardiographic complex of the subject Hm based on the signal transmitted from the electrocardiographic complex generation circuit 15 through the AND converter 31. The PWM signal generation section 35 generates a signal whose level changes in the shape of pulse according to a time axis as the detection signal SD. The PWM signal generation section 35 provides the detection signal SD to the detection signal input unit 40 through the I/O port 32.

The electrocardiographic calculation section 34 may be configured to generate and output the electrocardiographic complex as the biological information when the holding-state determination section 33 determines that the steering wheel SW is held with both the hands of the subject Hm. Further, the electrocardiographic calculation section 34 may be configured to generate information including at least a heart rate of the subject Hm based on the electrocardiographic complex and output the information as the biological information.

The detection signal input unit 40 includes a first input unit 41 and a second input unit 42. The first input unit 41 is configured to input a first detection signal SDr, which is one of the detection signals SD, to the first induction electrode ER. The second input unit 42 is provided to input a second detection signal SDI, which is one of the detection signals SD, to the second induction electrode EL.

The first input unit 41 includes a first voltage-dividing circuit 45, a coupling circuit 5, and a resistor R5. A first end of the first voltage-dividing circuit 45 is connected to the I/O port 32 of the microcomputer 30, and a second end of the first voltage-dividing circuit 45 is connected to the coupling circuit 5. An end of the coupling circuit 5 opposite to the first voltage-dividing circuit 45 is connected to the resistor R5. An end of the resistor R5 opposite to the coupling circuit 5 is connected to the first induction electrode ER.

The first voltage-dividing circuit 45 generates the first detection signal SDr by setting a potential of the detection signal SD outputted from the microcomputer 30 to a potential (hereinafter also referred to as the first potential) that is higher than a potential (hereinafter also referred to as the assumed potential) of a signal detected from a general subject Hm as the electrocardiographic complex.

The coupling circuit 5 permits an alternate current component of the first detection signal SDr generated from the first voltage-dividing circuit 45 to pass through. The coupling circuit 5 is provided by an RC circuit including a capacitor C5 and a resistor R3. The resistor R5 serves as a protective resistor.

Namely, the first input unit 41 provides the first detection signal SDr, which has a frequency higher than the frequency of the signal detected from the subject Hm as the electrocardiographic complex and a potential higher than the assumed potential, to the first induction electrode ER.

The second input unit 42 includes a second voltage-dividing circuit 46, a coupling circuit 6 and a resistor R6. The second voltage-dividing circuit 46, the coupling circuit 6 and the resistor R6 are connected to one another in a similar manner to the first voltage-dividing circuit 45, the coupling circuit 5 and the resistor R5. Therefore, a connection structure thereof will not be described in detail.

The second voltage-dividing circuit 46 generates the second detection signal SDI by setting the potential of the detection signal SD outputted from the microcomputer 30 to a potential that is higher than the assumed potential and different from the first potential, such as to a potential that is not an integral multiplication of the first potential. The coupling circuit 6 permits an alternate current component of the second detection signal SDI outputted from the second voltage-dividing circuit 46 to pass through. The coupling circuit 6 is provided by an RC circuit including a capacitor C6 and a resistor R4. The resistor R6 serves as a protective resistor.

Namely, the second input unit 42 provides the second detection signal DSI, which has a frequency higher than the frequency of the signal detected from the subject Hm as the electrocardiographic complex and a potential that is higher than the assumed potential and different from the first potential, to the second induction electrode EL.

The electrocardiographic complex generation circuit 15 is configured to generate the electrocardiographic complex of the subject Hm based on the differential signal Sd from the differential amplifier 10. The electrocardiographic complex generation circuit 15 includes a band-pass filter 16 and an amplifier 17. The band-pass filter 16 permits a signal that has a frequency (e.g., 0.3 to 35 hertz (Hz)) corresponding to a frequency of the electrocardiographic complex. The amplifier 17 amplifies the signal passing through the band-pass filter 16.

The holding-state detection circuit 20 is configured to generate the holding signal Sg, which indicates the holding state of the steering wheel SW, based on the differential signal Sd outputted from the differential amplifier 10. The holding-state detection circuit 20 includes a band-pass filter 21, a rectifier circuit 22 and an amplifier 23. The band-pass filter 21 permits a signal that has a frequency (e.g., 50 Hz or more) higher than the frequency (e.g., 0.3 to 35 Hz) of the electrocardiographic complex. The band-pass filter 21 may be provided by a high-pass filter. The rectifier circuit 22 rectifies the signal passing through the band-pass filter 21. The amplifier 23 amplifies the signal rectified in the rectifier circuit 22.

A frequency band of the signal passing through the band-pass filter 16 of the electrocardiographic complex generation circuit 15 and a frequency band of the signal passing through the band-pass filter 21 of the holding-state detection circuit 20 are different.

<Operation of Electrocardiograph>

Next, an operation of the electrocardiograph 1 will be described. In the electrocardiograph 1, the first detection signal SDr and the second detection signal SDl are normally inputted to the first induction electrode ER and the second induction electrode EL, respectively.

In a state where the body of the subject Hm is not in contact with the first induction electrode ER and the second induction electrode EL, the impedance of the first induction electrode ER and the impedance of the second induction electrode EL are infinity. Therefore, the differential signal Sd outputted from the differential amplifier 10 has a potential that is provided by amplifying the difference between the potential of the first detection signal SDr and the potential of the second detection signal SDl.

In a state where the body of the subject Hm is in contact with one of the first induction electrode ER and the second induction electrode EL, the impedance of the one with which the body of the subject Hm is in contact becomes small. Therefore, the potential of the signal transmitted from the one with which the body of the subject Hm is in contact to the differential amplifier 10 is zero. In this case, therefore, the differential signal Sd outputted from the differential amplifier 10 has a potential that is provided by amplifying the potential of the signal inputted to the differential amplifier 10 from the other one of the first induction electrode ER and the second induction electrode EL, which is not in contact with the body of the subject Hm.

In a state where the body of the subject Hm is in contact with the first induction electrode ER and the second induction electrode EL, the differential signal Sd has a potential that is provided by amplifying the potential of the electrocardiographic complex of the subject Hm.

<Advantageous Effects of the First Embodiment>

According to the electrocardiograph 1 of the first embodiment, the differential signal Sd outputted from the differential amplifier 10 varies in accordance with a contact state of the body of the subject Hm to the first induction electrode ER and the second induction electrode EL. Therefore, the electrocardiograph 1 of the first embodiment can determine that the body of the subject Hm is in contact with each of the first induction electrode ER and the second induction electrode EL.

The frequency of the detection signal SD is higher than the frequency of the signal detected from the subject Hm as the electrocardiographic complex. Therefore, the electrocardiographic complex and the detection signal SD can be easily separated through the filter. As such, an influence on measurement of the electrocardiographic complex of the subject Hm is reduced.

The signal level of the detection signal SD changes in the shape of pulse according to the time axis. The first detection signal SDr and the second detection signal SDl are generated by the first voltage-dividing circuit 45 and the second voltage-dividing circuit 46. Namely, in the electrocardiograph 1, the first detection signal SDr and the second detection signal SDl are easily generated by the microcomputer 30 and the first and second voltage-dividing circuits 45, 46.

The first detection signal SDr is inputted to the first induction electrode ER through the coupling circuit 5. Likewise, the second detection signal SDl is inputted to the second induction electrode EL through, the coupling circuit 6. Therefore, capacity of outputting the first detection signal SDr and the second detection signal SDl can be reduced.

As a result, when the body of the subject Hm is in contact with at least one of the first induction electrode ER and the second induction electrode EL, the potential can be properly approximated to "0". Accordingly, capacity of detecting the electrocardiographic complex improves.

In addition, the first detection signal SDr is inputted to the first induction electrode ER through the resistor R5. Likewise, the second detection signal SDl is inputted to the second induction electrode EL through the resistor R6. Therefore, the electrocardiographic complex of the subject Hm is further safely measured.

The first induction electrode ER and the second induction electrode EL are disposed in the steering wheel SW. Therefore, the electrocardiographic complex can be measured when the subject Hm holds the steering wheel SW. As such, the humans subject Hm, such as a passenger or a driver, may not need to be conscious of measurement of the electrocardiographic complex.

Furthermore, the frequency band of the signal passing through the band-pass filter, 16 of the electrocardiographic complex generation circuit 15 and the frequency band of the signal passing through the band-pass filter 21 of the holding-state detection circuit 20 are different. Therefore, the electrocardiographic complex and the holding signal are accurately detected.

(Second Embodiment)

A second embodiment of the present disclosure will be described with reference to FIGS. 4 through 6.

Hereinafter, an electrocardiograph 60 of the second embodiment will be described mainly with regard to a structure different from the electrocardiograph 1 of the first embodiment. Therefore, like parts are designated with like reference numbers, and a description thereof will not be repeated.

<Main Structure>

Figure 4:
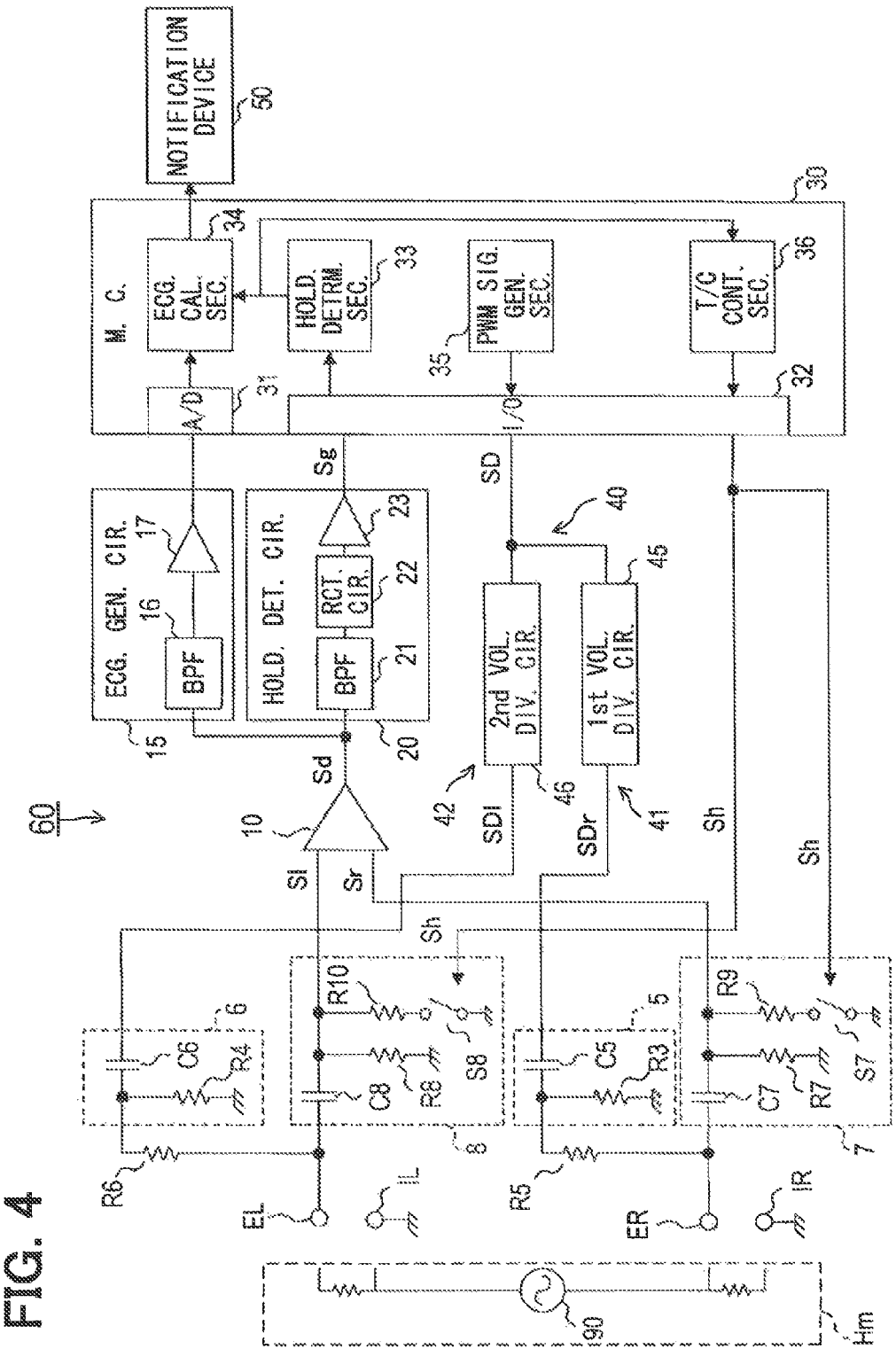
FIG. 4 is a block diagram of an electrocardiograph according to a second embodiment of the present disclosure.

Referring to FIG. 4, the electrocardiograph 60 generally includes the electrode unit 55, the detection signal input unit 40, the differential amplifier 10, the electrocardiographic complex generation circuit 15, the holding-state detection circuit 20, the microcomputer 30, and the notification device 50. In addition to these components, the electrocardiograph 60 includes a first time constant circuit 7 and a second time constant circuit 8 to make a part of the body of the subject Hm and the electrocardiograph 60 equipotential.

The first time constant circuit 7 is disposed between the first induction electrode ER and the differential amplifier 10. The first time constant circuit 7 mainly includes a CR circuit that includes a capacitor C7 and a resistor R7 connected in series to the capacitor C7. The first time constant circuit 7 further includes a resistor R9 and a switch S7 connected in series to the resistor R9. The resistor R9 has a resistance value smaller than a resistance value of the resistor R7.

The second time constant circuit 8 is disposed between the second induction electrode EL and the differential amplifier 10. Similar to the first time constant circuit 7, the second time constant circuit 8 includes a capacitor C8, a resistor R8, a resistor R10, and a switch S8. The resistor R8 is connected in series to the capacitor C8. The resistor R10 has a resistance value smaller than a resistance value of the resistor R8. The switch S8 is connected in series to the resistor R10.

The microcomputer 30 serves as a time constant control section 36 that outputs a time constant control signal Sh through the I/O port 32 for turning on the'switch S7 of the first time constant circuit 7 and the switch S8 of the second time constant circuit 8. The time constant control section 36 outputs the time constant control signal Sh when the holding-state determination section 33 determines that the steering wheel SW is held with both the hands.

<Operation of the Electrocardiograph>

Next, an operation of the electrocardiograph 60 will be described with reference to FIG. 5.

Figure 5:
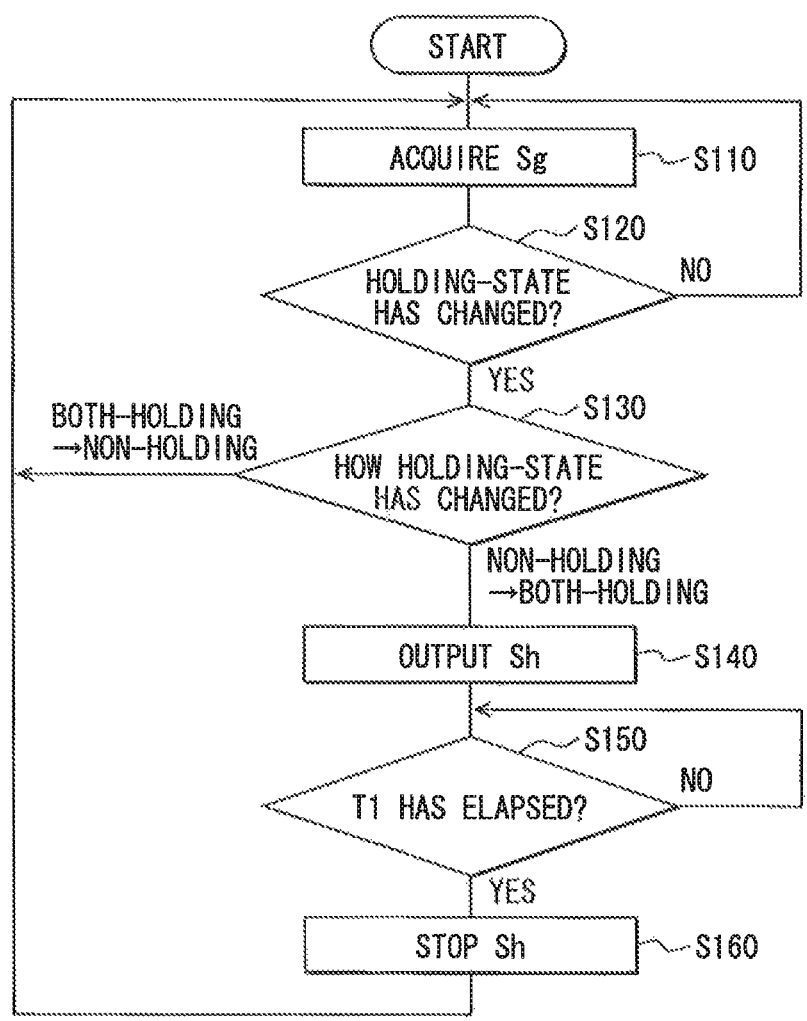
FIG. 5 is a diagram illustrating a flowchart of an operation of the electrocardiograph according to the second embodiment.

FIG. 5 is a flowchart illustrating an operation of the microcomputer 30 of the electrocardiograph 60. When being activated, the microcomputer 30 acquires the holding signal Sg from the holding-state detection circuit 20, at S110. The microcomputer 30 determines whether the holding state of the steering wheel SW indicated by the holding signal Sg has changed or not, at S120.

When it is determined that the holding state has not changed, corresponding to "No" at S120, the microcomputer 30 waits until the holding state changes. When it is determined that the holding state has changed, corresponding to "Yes" at S120, the microcomputer 30 proceeds the processing to S130.

At S130, the microcomputer 30 determines whether the change of the holding state corresponds to a change from a both-holding state to a non-holding state, or to a change from the non-holding state to the both-holding state. Here, the both-holding state means a state where the steering wheel SW is held with both the hands. Also, the non-holding state means a state where the steering wheel SW is not held with both the hands. That is, the non-holding state includes a state where the steering wheel SW is not held with both the hands, and a state where the steering wheel SW is held only with one hand.

When it is determined, at S130, that the holding state of the steering wheel SW has changed from the both-holding state to the non-holding state, the microcomputer 30 returns the processing to S110, and waits until the steering wheel SW is held with both the hands. When it is determined at S130, that the holding state of the steering wheel SW has changed from the non-holding state to the both-holding state, the microcomputer 30 begins to output the time constant control signal Sh at S140.

Next, at S150, the microcomputer 30 determines whether a predetermined time period T1 has elapsed since the output of the time constant control signal Sh was begun. When it is determined that the predetermined time period T1 has not elapsed, corresponding to "No" at S150, the microcomputer 30 waits until the predetermined time period T1 elapses since the output of the time constant control signal Sh was begun.

When it is determined that the predetermined time period T1 has elapsed since the output of the time constant control signal Sh was begun, corresponding to "Yes" at S150, the microcomputer 30 stops the output of the time constant control signal Sh at S160. Then, the microcomputer 30 returns the processing to S110.

In the second embodiment, the functions obtained by the operation according to the flowchart shown in FIG. 5 correspond to the function obtained by the holding-state determination section 33 and the function obtained by the time constant control section 36.

<Advantageous Effects of the Second Embodiment>

Figure 6:
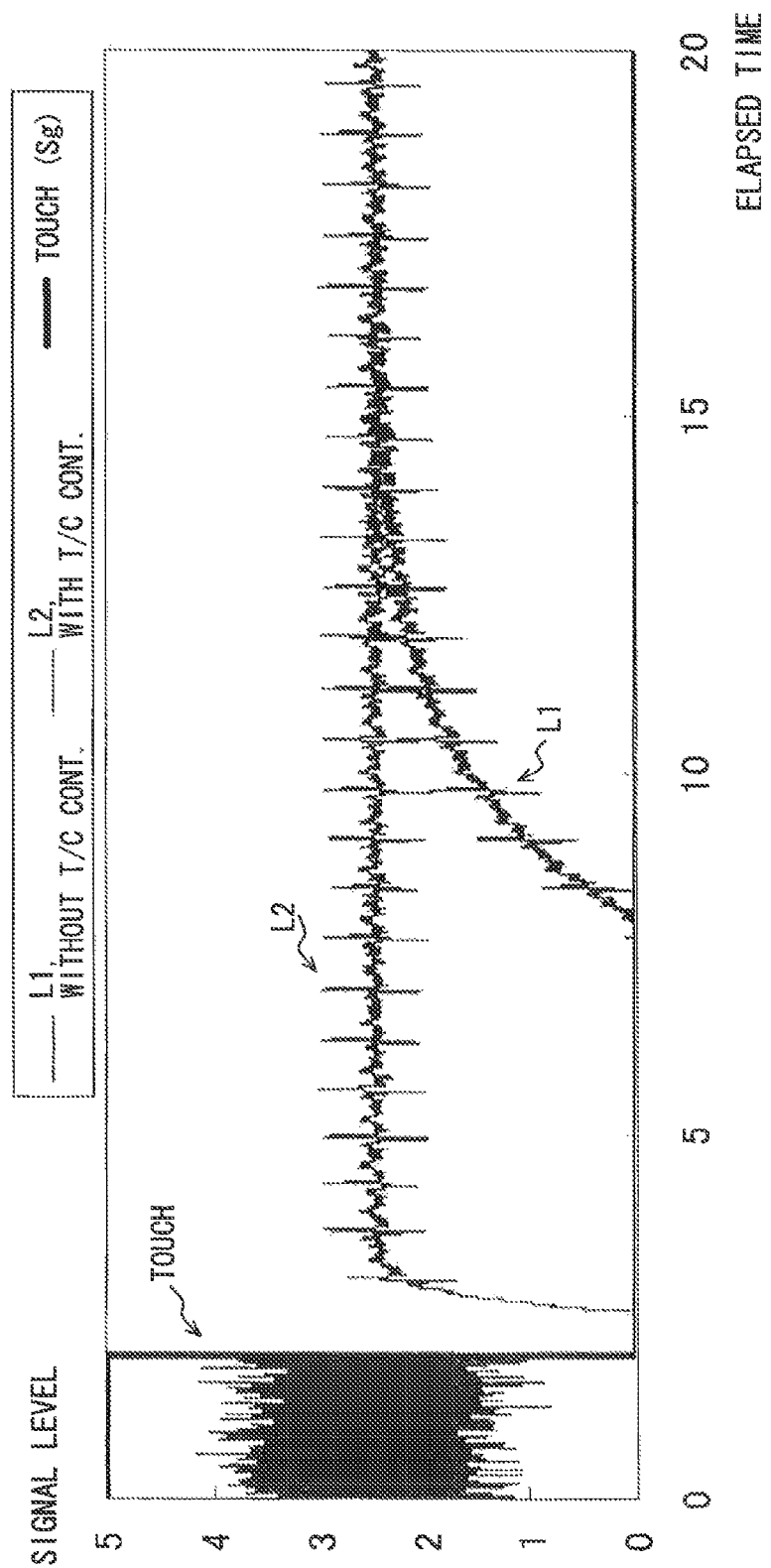
FIG. 6 is a diagram illustrating a graph for explaining an effect of the electrocardiograph according to the second embodiment.

FIG. 6 is a graph illustrating a time required to begin the measurement of the electrocardiographic complex of the subject Hm after the both-holding state of the steering wheel SW is detected by the holding-state determination section 33, with regard to the electrocardiograph 60 of the second embodiment and the electrocardiograph 1 of the first embodiment.

In FIG. 6, a "Touch" signal corresponds to the holding signal Sg. A timing where the "Touch" signal switches corresponds to a timing where the both-holding state is detected. Also, in FIG. 6, a line L1 indicates the result of the electrocardiograph 1 of the first embodiment, which does not have the time constant control. A line L2 indicates the result of the electrocardiograph 60 of the second embodiment, which has the time constant control.

As shown in FIG. 6, in the electrocardiograph 60 of the second embodiment, the time period from the detection of the both-holding state to the beginning of the measurement of the electrocardiographic complex of the subject Hm is shortened, as compared with the electrocardiograph 1 of the first embodiment.

(Other Embodiments)

The exemplary embodiments of the present disclosure have been described hereinabove. However, the present disclosure is not limited to the embodiments described above, but may be implemented in various other ways without departing from the spirit of the present disclosure.

In the embodiment described above, the first detection signal SDr and the second detection signal SDl have the same frequency, but have different potentials. The first detection signal SDr and the second detection signal SDl are not limited to the above, and may have any other properties as long as the holding state of the steering wheel SW can be properly determines as a both-holding state where the steering wheel SW is held with both the hands, a one hand-holding state where the steering wheel SW is held with right hand or left hand, and a non-holding state where the steering wheel SW is not held with the hands.

For example, the first detection signal SDr and the second detection signal SDl may at least have potentials higher than the assumed potential that is assumed as the potential of the electrocardiographic complex. In such a case, it is possible to properly determine whether the body of the subject Hm is in contact with the first induction electrode ER and the second induction electrode EL based on a signal difference between the signal outputted from the first induction electrode ER and the second induction electrode EL.

In addition to or alternative to the potentials described above, the first detection signal SDr and the second detection signal SDl may have frequencies higher than an assumed frequency that is assumed as the frequency of the electrocardiographic complex. In such a case, the influence on the measurement of the electrocardiographic complex can be reduced.

The first detection signal SDr and the second detection signal SDl may be pulse signals whose potentials vary according to a time axis. In such a case, the first detection signal SDr and the second detection signal SDl are easily generated by using the microcomputer 30 and the first and second voltage-dividing circuits 45, 46.

For example, the first detection signal SDr and the second detection signal SDl may have the same phase, but the potential of the second detection signal SDl may be lower than the potential of the first detection signal SDr. In such a case, the signal difference, that is, a potential difference of the signal outputted from the first induction electrode ER and the signal outputted from the second induction electrode EL is different between a case where the body of the subject Hm is in contact with only the first induction electrode ER and a case where the body of the subject Hm is in contact with only the second induction electrode EL. Therefore, the contact state of the body to the first induction electrode ER and the second induction electrode EL can be properly determined.

For example, it may be possible to differentiate the phase of the first detection signal SDr and the phase of the second detection signal SDl from each other, alternative to or in addition to the property difference described above. For example, the phase of the first detection signal SDr and the phase of the second detection signal SDl may be shifted by 180 degrees or less from each other. In such a case, the signal difference is different between a case where the body of the subject Hm is in contact with only the first induction electrode ER and a case where the body of the subject Hm is in contact with only the second induction electrode EL. Therefore, the contact state of the body to the first induction electrode ER and the second induction electrode EL can be properly determined. To realize these properties, for example, the first input unit 41 or the second input unit 42 may have a signal delay circuit for shifting (e.g., delaying) the phase of one of the first detection signal SDr and the second detection signal SDI from the other.

For example, it may possible to differentiate the frequency of the first detection signal SDr and the frequency of the second detection signal SDI from each other, alternative to or in addition to the property difference described above. In such a case, the signal difference of the case where only the first induction electrode ER is in contact with the body of the subject Hm and the signal difference of the case where only the second induction electrode EL is in contact with the body of the subject Hm are different in frequency. Therefore, by detecting the frequency of the signal difference, the contact state of the body to the first induction electrode ER and the second induction electrode EL can be properly determined. To realize these properties, for example, the PWM signal generation section 35 may be provided for each of the first detection signal SDr and the second detection signal SDI. Further, the circuit for determining the holding state may be provided for each of the first detection signal SDr and the second detection signal SDI.

The first induction electrode ER is disposed adjacent to the first reference electrode IR, so that the body of the subject Hm contacts the first induction electrode ER together with the first reference electrode IR. Likewise, the second induction electrode EL is disposed adjacent to the second reference electrode IL, so that the body of the subject Hm contacts the second induction electrode EL together with the second reference electrode IL In the embodiments described above, the first induction electrode ER, the second induction electrode EL, the first reference electrode IR and the second reference electrode IL are all disposed in the steering wheel SW. However, the arrangement positions of the first induction electrode ER, the second induction electrode EL, the first reference electrode EL and the second reference electrode IL are not limited in the steering wheel SW.

Figure 7A:
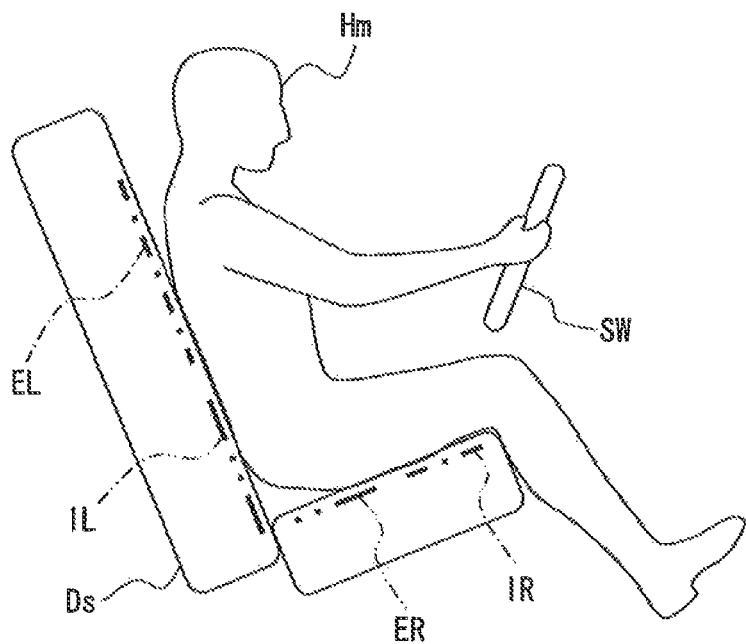
FIG. 7A is a diagram illustrating an example of arrangement of electrodes of an electrocardiograph according to another embodiment.

For example, as shown in FIG. 7A, all the first induction electrode ER, the second induction electrode EL, the first reference electrode IR and the second reference electrode IL may be disposed in the seat of the vehicle, such as a drivers seat Ds.

Figure 7B:
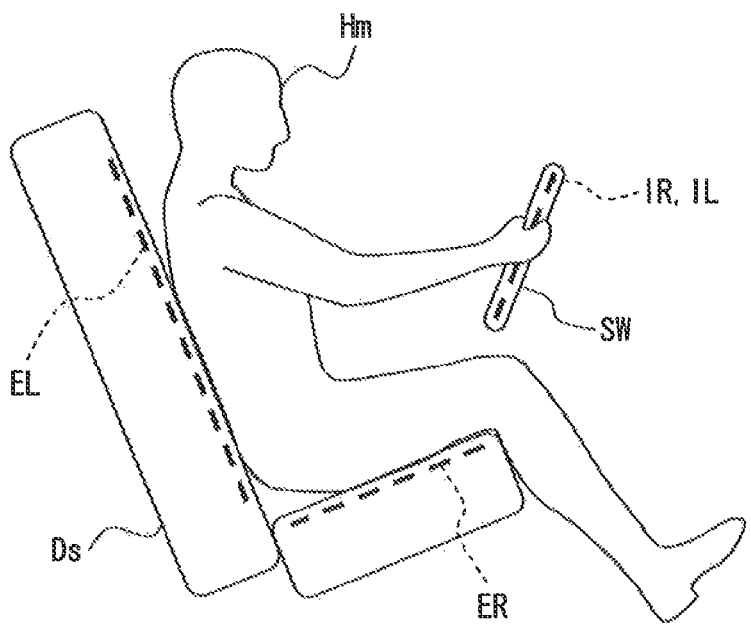
FIG. 7B is a diagram illustrating an example of arrangement of electrodes of an electrocardiograph according to further another embodiment.
Figure 8A:
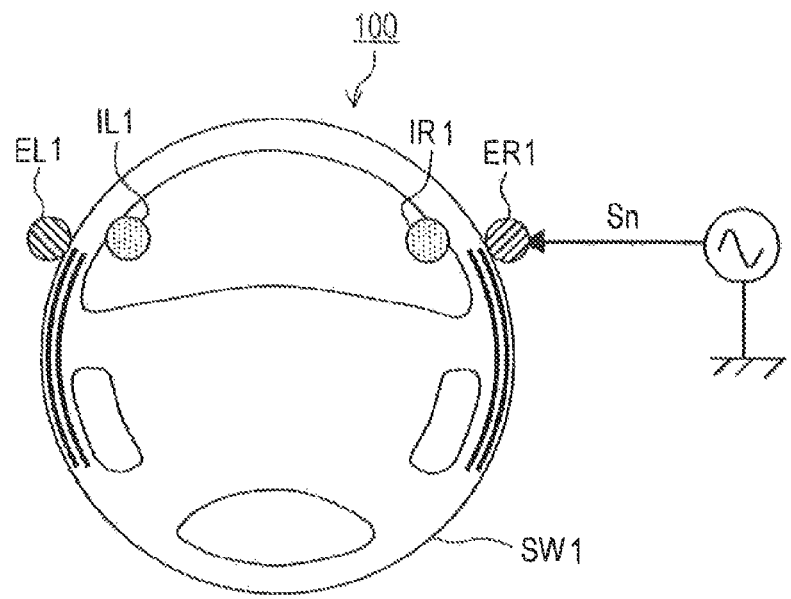
FIG. 8A is a diagram illustrating a plan view of a steering wheel equipped with electrodes of an assumed electrocardiograph according to a related art.
Figure 8B:
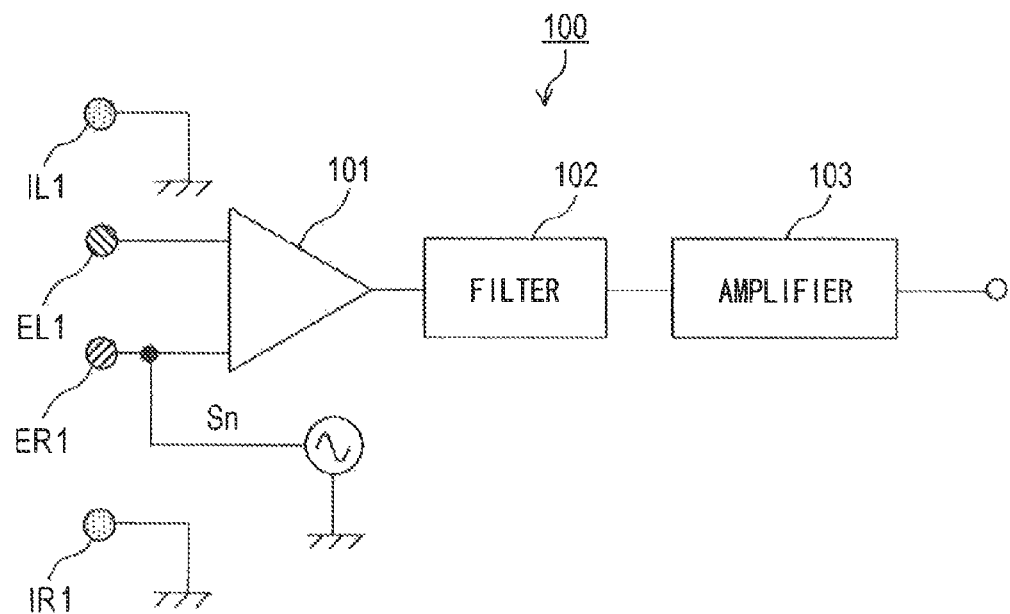
FIG. 8B is a block diagram of the assumed electrocardiograph according to the related art.

As another example, as shown in FIG. 7B, the first induction electrode ER and the second induction electrode EL may be disposed in the seat of the vehicle, such as a driver's seat Ds, and the first reference electrode IR and the second reference electrode IL may be disposed in the steering wheel SW.

Namely, the first induction electrode ER, the second induction electrode EL, the first reference electrode IR and the second reference electrode IL may be disposed in any positions as long as the electrocardiograph 1, 60 can detect that the subject Hm is in a state suitable for measurement of the electrocardiographic complex.

The first induction electrode ER, the second induction electrode EL, the first reference electrode IR and the second reference electrode IL are not limited to electrodes that induce a signal inputted thereto through a resistance coupling, but may be electrodes that induce a signal inputted thereto through a capacity coupling.

<Correspondence Between Exemplary Embodiments and Claims>

In the embodiments described above, the differential amplifier 10 may correspond to a signal difference generation section. The electrocardiographic complex generation circuit 15 and the electrocardiographic calculation section 34 may correspond to an electrocardiographic detection section. The PWM signal generation section 35 and the detection signal input unit 40 may correspond to a signal applying section. The holding-state detection circuit 20 and the holding-state determination section 33 may correspond to a contact detection section.

Further, the first time constant circuit 7 and the second time constant circuit 8 may correspond to a first time constant setting section and a second time constant setting section. The time constant control section 36 may correspond to a command outputting section. The detection signal SD and the first detection signal SDr may correspond to a first signal. The detection signal SD and the second detection signal SDI may correspond to a second signal.

While only the selected exemplary embodiments have been chosen to illustrate the present disclosure, it will be apparent to those skilled in the art from this disclosure that various changes and modifications can be made therein without departing from the scope of the disclosure as defined in the appended claims. Furthermore, the foregoing description of the exemplary embodiments according to the present disclosure is provided for illustration only, and not for the purpose of limiting the disclosure as defined by the appended claims and their equivalents.

What is claimed is:

1. An electrocardiograph comprising:
    a first induction electrode inducting a first signal applied thereto;
    a second induction electrode inducting a second signal applied thereto;
    a first reference electrode associated with the first induction electrode as an indifferent electrode;
    a second reference electrode associated with the second induction electrode as an indifferent electrode;
    a signal difference generation section generating a potential difference between a signal outputted from the first induction electrode and a signal outputted from the second induction electrode as a signal difference;
    an electrocardiographic detection section detecting an electrocardiographic complex of a subject based on the signal difference generated by the signal difference generation section;
    a signal applying section applying the first signal to the first induction electrode and the second signal to the second induction electrode, the first signal having a property different from the electrocardiographic complex, the second signal having a property different from the electrocardiographic complex and the first signal; and
    a contact detection section detecting a contact state of the subject to the first induction electrode and the second induction electrode based on the signal difference generated by the signal difference generation section.

2. The electrocardiograph according to claim 1, wherein
    the first signal has a potential higher than an assumed potential of the electrocardiographic complex, and
    the second signal has a potential higher than the assumed potential of the electrocardiographic complex.

3. The electrocardiograph according to claim 1, wherein
    the first signal has a frequency higher than an assumed frequency of the electrocardiographic complex, and the second signal has a frequency higher than the assumed frequency of the electrocardiographic complex.

4. The electrocardiograph according to claim 1, wherein
the first signal has a pulse shape where a potential of the first signal changes in a shape of pulse along a time axis, and
the second signal has a pulse shape where a potential of the second signal changes in a shape of pulse along a time axis.

5. The electrocardiograph according to claim 1, wherein the first signal and the second signal have a same phase, and the second signal has a potential lower than a potential of the first signal.

6. The electrocardiograph according to claim 1, wherein the first signal has a phase different from a phase of the second signal.

7. The electrocardiograph according to claim 1, wherein the first signal has a frequency different from a frequency of the second signal.

8. The electrocardiograph according to claim 1, further comprising:
a first capacitor disposed between the signal applying section and the first induction electrode; and
a second capacitor disposed between the signal applying section and the second induction electrode, wherein
the signal applying section applies the first signal to the first induction electrode through the first capacitor, and
the signal applying section applies the second signal to the second induction electrode through the second capacitor.

9. The electrocardiograph according to claim 1, further comprising:
a first protective resistor disposed between the signal applying section and the first induction electrode; and
a second protective resistor disposed between the signal applying section and the second induction electrode, wherein
the signal applying section applies the first signal to the first induction electrode through the first protective resistor, and
the signal applying section applies the second signal to the second induction electrode through the second protective resistor.

10. The electrocardiograph according to claim 1, wherein the electrocardiographic detection section detects the electrocardiographic complex of the subject when the contact detection section has detected that the subject is in contact with the first induction electrode and the second induction electrode.

11. The electrocardiograph according to claim 1, further comprising:
a time constant setting section disposed between the signal difference generation section and each of the first induction electrode and the second induction electrode, the time constant setting section including a CR circuit that includes a resistor and a capacitor connected in series to the resistor, the time constant setting section setting a time constant of the CR circuit in accordance with a command inputted to the time constant setting section; and
a command outputting section outputting the command to the time constant setting section to shorten the time constant of the CR circuit when the contact detection section has detected that the subject is in contact with the first induction electrode and the second induction electrode.

12. The electrocardiograph according to claim 1, wherein the electrocardiographic complex generation section generates biological information indicating a condition of the subject when the contact detection section has detected that the subject is in contact with the first induction electrode and the second induction electrode.

13. The electrocardiograph according to claim 1, wherein the first induction electrode is disposed adjacent to the first reference electrode, and
the second induction electrode is disposed adjacent to the second reference electrode.

14. The electrocardiograph according to claim 1, wherein the first induction electrode and the second induction electrode are disposed in one of a steering wheel of a vehicle and a seat of the vehicle.

15. The electrocardiograph according to claim 1, wherein the first induction electrode and the second induction electrode are disposed in a driver's seat of a vehicle, and
the first reference electrode and the second reference electrode are disposed in a steering wheel of the vehicle.

* * * * *